(12) United States Patent
Backer et al.

(10) Patent No.: US 6,534,668 B2
(45) Date of Patent: Mar. 18, 2003

(54) PREPARATION OF SULFUR-CONTAINING ORGANOSILICON COMPOUNDS USING A BUFFERED PHASE TRANSFER CATALYSIS PROCESS

(75) Inventors: Michael Wolfgang Backer, Barry, Vale of Glamorgan (GB); Howard Marvin Bank, Freeland, MI (US); John Michael Gohndrone, Midland, MI (US); William Charles Maki, Midland, MI (US); Charles Edmund Skinner, Midland, MI (US); Anil Kumar Tomar, Midland, MI (US); Hongjun Yue, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/895,719

(22) Filed: Jun. 29, 2001

(65) Prior Publication Data

US 2003/0013901 A1 Jan. 16, 2003

(51) Int. Cl.$^7$ .............................. C07F 7/08; C07F 7/18
(52) U.S. Cl. ......................................................... 556/427
(58) Field of Search ......................................... 556/427

(56) References Cited

U.S. PATENT DOCUMENTS

| | | | |
|---|---|---|---|
| 3,590,065 A | 6/1971 | Rakus et al. .............. | 260/448.8 |
| 4,082,790 A | 4/1978 | Speier ....................... | 260/448.8 |
| 4,401,826 A | 8/1983 | Selin ........................... | 556/429 |
| 4,556,724 A | 12/1985 | Seiler et al. .................. | 556/429 |
| 5,107,009 A | 4/1992 | Rauleder et al. ............ | 556/429 |
| 5,399,739 A | 3/1995 | French et al. ............... | 556/427 |
| 5,405,985 A | 4/1995 | Parker et al. ............... | 556/427 |
| 5,466,848 A | 11/1995 | Childress .................... | 556/427 |
| 5,468,893 A | 11/1995 | Parker et al. ............... | 556/427 |
| 5,489,701 A | 2/1996 | Childress et al. ........... | 556/427 |
| 5,583,245 A | 12/1996 | Parker et al. ............... | 556/427 |
| 5,596,116 A | 1/1997 | Childress et al. ........... | 556/427 |
| 5,663,396 A | 9/1997 | Musleve et al. ............. | 556/427 |
| 5,840,952 A | 11/1998 | Kudo et al. .................. | 556/429 |
| 5,859,275 A | 1/1999 | Munzenberg et al. ........ | 556/427 |
| 5,892,085 A | 4/1999 | Munzenberg et al. ........ | 552/427 |
| 5,936,112 A | 8/1999 | Gobel et al. ................. | 556/427 |
| 6,066,752 A | 5/2000 | Takata et al. ................ | 556/427 |
| 6,140,524 A | 10/2000 | Ichinohe et al. ............. | 556/427 |
| 6,384,256 B1 * | 5/2002 | Backer et al. ............... | 556/427 |

* cited by examiner

*Primary Examiner*—Paul F. Shaver
(74) *Attorney, Agent, or Firm*—Alan Zombeck; Jim L. De Cesare

(57) ABSTRACT

A process for the production of sulfur containing organosilicon compounds of the formula:

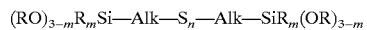

$$(RO)_{3-m}R_mSi-Alk-S_n-Alk-SiR_m(OR)_{3-m}$$

where

R is independently a monovalent hydrocarbon of 1 to 12 carbon atoms; Alk is a divalent hydrocarbon of 1 to 18 carbon atoms;

m is an integer of 0 to 2, n is a number from 1 to 8;

based on phase transfer catalysis techniques is disclosed. The process comprises reacting:

(A) a sulfide compound having the formula $M_2S_n$ or MHS, where H is hydrogen, M is ammonium or an alkali metal, n is as defined above, with (B) a silane compound of the formula;

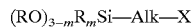

$$(RO)_{3-m}R_mSi-Alk-X$$

where X is Cl, Br or I, and m is the same as above, and optionally, (C) sulfur in the presence of a phase transfer catalyst and an aqueous phase containing a buffer.

The improvement of the present invention is characterized by adding a buffer to the aqueous phase, which minimizes or prevents gelling of the sulfur containing organosilicon compounds. The present invention also teaches a process for the production of sulfur containing organosilicon compounds by controlling the pH of the aqueous phase.

39 Claims, No Drawings

PREPARATION OF SULFUR-CONTAINING ORGANOSILICON COMPOUNDS USING A BUFFERED PHASE TRANSFER CATALYSIS PROCESS

FIELD OF THE INVENTION

This invention relates to a process for the production of sulfur containing organosilicon compounds by phase transfer catalysis techniques. The process involves reacting a sulfide, and optionally sulfur, with a silane compound in the presence of a phase transfer catalyst and aqueous phase containing a buffer.

BACKGROUND OF THE INVENTION

Sulfur containing organosilicon compounds are useful as reactive coupling agents in a variety of commercial applications. In particular, sulfur containing organosilicon compounds have become essential components in the production of tires based on rubber vulcanates containing silica. The sulfur containing organosilicon compounds improve the physical properties of the rubber vulcanates containing silica resulting in automotive tires with improved abrasion resistance, rolling resistance, and wet skidding performance. The sulfur containing organosilicon compounds can be added directly to the rubber vulcanates containing silica, or alternately, can be used to pre-treat the silica prior to addition to the rubber vulcanate composition.

Numerous methods have been described in the art for the preparation of sulfur containing organosilicon compounds. For example, U.S. Pat. No. 5,399,739 by French et al. describes a method for making sulfur-containing organosilanes by reacting an alkali metal alcoholate with hydrogen sulfide to form an alkali metal hydrosulfide, which is subsequently reacted with an alkali metal to provide an alkali metal sulfide. The resulting alkali metal sulfide is then reacted with sulfur to provide an alkali metal polysulfide which is then finally reacted with a silane compound of the formula X—$R^2$—Si($R^1$)$_3$, where X is either chlorine or bromine to produce the sulfur-containing organosilane.

U.S. Pat. Nos. 5,466,848, 5,596,116, and 5,489,701 describe processes for the preparation of silane polysulfides. The '848 patent process is based on first producing sodium sulfide by the reaction of hydrogen sulfide with sodium ethoxylate. The sodium sulfide is then reacted with sulfur to form the tetrasulfide, which is subsequently reacted with chloropropyltriethoxysilane to form 3,3'-bis (triethoxysilylpropyl) tetrasulfide. The '116 patent teaches a process for the preparation of polysulfides, without the use of hydrogen sulfide, by reacting a metal alkoxide in alcohol with elemental sulfur, or by reacting sodium metal with elemental sulfur and an alcohol, with a halohydrocarbylalkoxysilane such as chloropropyltriethoxysilane. The '701 patent claims a process for the preparation of silane polysulfides by contacting hydrogen sulfide gas with an active metal alkoxide solution and subsequently reacting the reaction product with a halohydrocarbylalkoxysilane such as chloropropyltriethoxysilane.

U.S. Pat. No. 5,892,085 describes a process for the preparation of high purity organosilicon disulphanes. U.S. Pat. No. 5,859,275 describes a process for the production of bis (silylorganyl) polysulphanes. Both the '085 and '275 patents describe anhydrous techniques involving the direct reaction of a haloalkoxysilane with a polysulphide.

U.S. Pat. No. 6,066,752 teaches a process for producing sulfur-containing organosilicon compounds by reacting sulfur, an alkali metal, and a halogenalkoyxsilane in the absence of a solvent or in the presence of an aprotic solvent.

Most recently, U.S. Pat. No. 6,140,524 describes a method for preparing short chain polysulfide silane mixtures of the formula $(RO)_3SiC_3H_6S_nC_3H_6Si(RO)_3$ having a distribution where n falls in the range of $2.2 \leq n \leq 2.8$. The '524 method reacts metal polysulfides, typically $Na_2S_n$ with a halogenopropyltrialkoxysilane having the formula $(RO)_3SiC_3H_6X$ wherein X is a halogen, in alcohol solvent.

Alternative processes for the preparation of sulfur-containing organosilanes have been taught in the art based on the use of phase transfer catalysis techniques. Phase transfer catalysis techniques overcome many of the practical problems associated with the aforementioned prior art processes for producing sulfur-containing organosilicon compounds. Many of these problems are related to the use of solvents. In particular, the use of ethyl alcohol can be problematic because of its low flash point. Additionally, it is difficult to obtain and maintain anhydrous conditions necessary in many of the aforementioned prior art processes on an industrial scale.

Phase transfer catalysis techniques for producing sulfur-containing organosilicon compounds are taught for example in U.S. Pat. Nos. 5,405,985, 5,663,396, 5,468,893, and 5,583,245. While these patents teach new processes for the preparation of sulfur containing organosilicon compounds using phase transfer catalysis, there still exist many practical problems with the use of phase transfer techniques at an industrial scale. For example, there is a need to control the reactivity of the phase transfer catalyst in the preparation of sulfur-containing organosilanes so as to provide efficient, yet safe reactions, that can be performed on an industrial scale. Furthermore, there is a need to improve the final product stability, appearance and purity. In particular, the phase transfer catalysis process of the prior art results in final product compositions containing high quantities of un-reacted sulfur species. These un-reacted sulfur species can precipitate in stored products with time causing changes in product sulfide distribution.

The need to improve product quality is of particular importance when an alkali metal or ammonium hydrogen sulfide is used as a starting material in phase transfer catalysis techniques. In these reactions, dangerous and odorous hydrogen sulfide is produced in side reactions. Product compositions containing even minor amounts of hydrogen sulfide deter their use in large scale industrial processes.

Yet another problem associated with the use of phase transfer catalysis techniques for producing sulfur containing organosilicon compounds is gelation, caused by the hydrolysis of the alkoxy groups on the organosilicon compound, or starting silane reactant, with the aqueous phase reactants.

It is therefore an object of the present invention to provide an improved process for the production of sulfur containing organosilicon compounds based on phase transfer catalysis techniques.

It is a further object of the present invention to provide a process for producing sulfur containing organosilicon compounds based on phase transfer catalysis techniques that result in a final product composition of greater stability, purity, and appearance.

It is yet a further object of the present invention to provide a process for producing sulfur containing organosilicon compounds based on phase transfer techniques using a hydrosulfide compound that minimizes or eliminates hydrogen sulfide as a side product.

It is still yet a further object of the present invention to provide a process for producing sulfur containing organosilicon compounds based on phase transfer techniques where gelation of starting materials or resulting products is minimized or eliminated.

SUMMARY OF THE INVENTION

The present invention provides a process for the production of sulfur containing organosilicon compounds by a buffered phase transfer catalysis techniques. Sulfur containing organosilicon compounds are prepared by the process of the present invention by reacting ammonium hydrosulfide or an alkali metal hydrosulfide, and optionally sulfur, with a silane compound having the formula

where X is Cl, Br or I,
in the presence of a phase transfer catalyst and an aqueous phase containing a buffer.

The improvement of the present invention is characterized by adding a buffer to the aqueous phase. The present invention also provides an improved process for the production of sulfur containing organosilicon compounds by controlling the pH of the aqueous phase.

The present invention also encompasses the organosilicon compounds produced by the improved process.

DETAILED DESCRIPTION OF THE INVENTION

The present invention is a process for the production of organosilicon compounds of the formula:

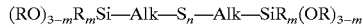

where
R is independently a monovalent hydrocarbon of 1 to 12 carbon
atoms; Alk is a divalent hydrocarbon of 1 to 18 carbon atoms;
m is an integer of 0 to 2, n is a number from 1 to 8;
comprising reacting:
(A) a sulfide compound having the formula $M_2S_n$ or MHS,
where H is hydrogen, M is ammonium or an alkali metal,
n is as defined above, with
(B) a silane compound of the formula;

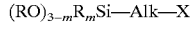

where X is Cl, Br or I, and m is the same as above, and optionally,
(C) sulfur
in the presence of a phase transfer catalyst and an aqueous phase containing a buffer.

Examples of sulfur containing organosilicon compounds which may be prepared in accordance with the present invention are described in U.S. Pat. Nos. 5,405,985, 5,663, 396, 5,468,893, and 5,583,245, which are hereby incorporated by reference. The preferred sulfur containing organosilicon compounds which are prepared in accordance with the present invention are the 3,3'-bis(trialkoxysilylpropyl) polysulfides. The most preferred compounds are 3,3'-bis (triethoxysilylpropyl) disulfide and 3,3'-bis (triethoxysilylpropyl) tetrasulfide.

Sulfide compounds of the formula $M_2S_n$ or MHS can be used as component (A) in the reaction step of the process of the present invention, where M represents an alkali metal or ammonium group and H represents hydrogen. Representative alkali metals include lithium, potassium, sodium, rubidium, or cesium. Preferably M is sodium. Generally, MHS compounds are used preferentially when the average value of n in the resulting product formula, $(RO)_{3-m}R_mSi$—Alk—$S_n$—Alk—$SiR_m(OR)_{3-m}$ is desired to be 2. Examples of the MHS compound include NaHS, KHS, and $NH_4HS$. When the sulfide compound is an MHS compound, NaHS is preferred. Specific examples of the NaHS compound include NaHS flakes (containing 71.5–74.5% NaHS) and NaHS liquors (containing 45–60% NaHS) from PPG of Pittsburgh, Pa. $M_2S_n$ compounds are used preferentially when the average value of n in the resulting product formula, $(RO)_{3-m}R_mSi$—Alk—$S_n$—Alk—$SiR_m(OR)_{3-m}$ is desired to be 4. Specific examples of compounds of $M_2S_n$ include $Na_2S$, $K_2S$, $Cs_2S$, $(NH_4)_2S$, $Na_2S_2$, $Na_2S_3$, $Na_2S_4$, $Na_2S_6$, $K_2S_2$ $K_2S_3$, $K_2S_4$, $K_2S_6$, and $(NH_4)_2S_2$. Preferably the sulfide compound is $Na_2S$. A particular preferred sulfide compound is sodium sulfide flakes (containing 60–63% $Na_2S$) from PPG of Pittsburgh, Pa.

Component (B) in the reaction step of the process of the present invention is a silane compound of the formula;

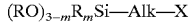

R can independently be any hydrocarbon group containing 1 to 12 carbon atoms. Thus, examples of R can include methyl, ethyl, propyl, butyl, isobutyl, cyclohexyl, or phenyl. Preferably, R is a methyl or ethyl group. In the formula $(RO)_{3-m}R_mSi$—Alk—X, m is an integer and can have a value from 0 to 2. Preferably, m is equal to 0. Alk is a divalent hydrocarbon group containing 1 to 18 carbons. Alk can be for example; ethylene, propylene, butylene, or isobutylene. Preferably Alk contains 2 to 4 carbons, and most preferable Alk is a propylene group. X is a halogen atom selected from chlorine, bromine, or iodine. Preferably X is chlorine. Examples of silane compounds that may be used in the present invention include chloropropyl triethoxy silane, chloropropyl trimethoxy silane, chloroethyl triethoxy silane, chlorobutyl triethoxy silane, chloroisobutylmethyl diethoxy silane, chloroisobutylmethyl dimethoxy silane, chloropropyldimethyl ethoxy silane. Preferably, the silane compound of the present invention is chloropropyl triethoxy silane (CPTES).

Sulfur can also be added to the reaction step on the process of the present invention as an optional component, (C). The sulfur used in the reaction of the present invention is elemental sulfur. The type and form are not critical and can include those commonly used. An example of a suitable sulfur material is 100 mesh refined sulfur powder from Aldrich, Milwaukee Wis.

The amount of sulfur and sulfide compound used in the process of the present invention can vary, but preferably the molar ratio of $S/M_2S_n$ or S/MHS ranges from 0.3 to 5. The molar ratio of sulfur/sulfide compound can be used to affect the final product distribution, that is the average value of n in the formula, $(RO)_{3-m}R_mSi$—Alk—$S_n$—Alk—$SiR_m$ $(OR)_{3-m}$. When the average value of n is desired to be 4 in the product formula, $(RO)_{3-m}R_mSi$—Alk—$S_n$—Alk—$SiR_m$ $(OR)_{3-m}$, the preferred range for the ratio of sulfur/sulfide compound is from 2.7 to 3.2. When the average value of n is desired to be 2 in the product formula, $(RO)_{3-m}R_mSi$—Alk—$S_n$—Alk—$SiR_m(OR)_{3-m}$, the preferred range for the ratio of sulfur/sulfide compound is from 0.8 to 1.2.

The silane compound, $(RO)_{3-m}R_mSi$—Alk—X, can be reacted in the presence of or absence of a solvent with the sulfide compound, or alternatively with the sulfide compound and sulfur in combination, as described above. The silane compound can also be dispersed in an organic solvent to form an organic phase. Representative examples of organic solvents include toluene, xylene, benzene, heptane, octane, nonane, decane, chlorobenzene and the like. When an organic solvent is used, the preferred organic solvent is toluene.

When conducting the reaction of the present invention, preferably the silane compound is reacted directly with the sulfide compound and sulfur in combination as described above.

The amount of the silane compound $(RO)_{3-m}R_mSi$—Alk—X used in the process of the present invention can vary. An example of a suitable molar range includes from 1/10 to 10/1 based on the amount of sulfide compound used. When the average value of n is desired to be 4 in the product formula, $(RO)_{3-m}R_mSi$—Alk—$S_n$—Alk—$SiR_m(OR)_{3-m}$, the silane compound $(RO)_{3-m}R_mSi$—Alk—X is used from 2.0 to 2.10 in molar excess of the $M_2S_n$ sulfide compound, with a range of 2.01 to 2.06 being the most preferable. When the average value of n is desired to be 2 in the product formula, $(RO)_{3-m}R_mSi$—Alk—$S_n$—Alk—$SiR_m(OR)_{3-m}$, the silane compound $(RO)_{3-m}R_mSi$—Alk—X is used from 1.8 to 2.10 in molar excess of the MHS sulfide compound, with a range of 1.9 to 2.0 being the most preferable.

The phase transfer catalysts operable in the present invention are the quaternary onium cations. Preferred examples of the quaternary onium cations as phase transfer catalysts are described in U.S. Pat. No. 5,405,985, which is hereby incorporated by reference. Preferably, the quaternary onium cation is tetrabutyl ammonium bromide or tetrabutyl ammonium chloride. The most preferred quaternary onium salt is tetrabutyl ammonium bromide. A particularly preferred quaternary onium salt is tetrabutyl ammonium bromide (99%) from Aldrich Chemical of Milwaukee, Wis.

The amount of the phase transfer catalyst used in the process may vary. Preferably the amount of phase transfer catalyst is from 0.1 to 10 weight %, and most preferably from 0.5 to 2 weight % based on the amount of silane compound used.

The phase transfer catalyst may be added to the reaction at any time. Preferably, the phase transfer catalyst is added to the aqueous phase prior the reaction step of the process of the present invention.

The reaction of the present invention is conducted in the presence of an aqueous phase containing a buffer. The buffer can be a single compound such as an alkali metal salt of a phosphate, a hydrogen phosphate, a dihydrogen phosphate, a carbonate, a hydrogen carbonate, or a borate, or combinations thereof. Examples of buffers include; $Na_3PO_4$, $Na_2HPO_4$, $NaH_2PO_4$, $Na_2CO_3$, $NaHCO_3$, and $NaB_4O_7$. Preferably, the buffer is selected from $Na_3PO_4$, $Na_2CO_3$, or $K_2CO_3$ When the average value of n is desired to be 4 in the product formula, $(RO)_{3-m}R_mSi$—Alk—$S_n$—Alk—$SiR_m(OR)_{3-m}$, the preferred buffer is $Na_3PO_4$. When the average value of n is desired to be 2 in the product formula, $(RO)_{3-m}R_mSi$—Alk—$S_n$—Alk—$SiR_m(OR)_{3-m}$, the preferred buffer is $Na_2CO_3$ or $K_2CO_3$.

The amount of the buffer added to the aqueous phase can vary, but generally is added in molar amounts equal to or greater than the number of moles of $M_2S_n$ or MHS.

In a preferred embodiment of the present invention, the sulfide compound, the phase transfer catalyst, the buffer, water, and optionally sulfur, are mixed together to form an intermediate reaction product. This reaction can be conducted at a variety of temperatures, but generally in the range of 40–100° C. Preferably, the reaction is conducted at a temperature ranging from 65–95° C. Generally, the first step can be conducted at various pressures, but preferably the first step reaction is conducted at atmospheric pressure. The time needed for the reaction of the first step to occur is not critical, but generally ranges from 5 to 30 minutes. The intermediate reaction product is then reacted with the silane compound, $(RO)_{3-m}R_mSi$—Alk—X. The time needed for the reaction of the intermediate reaction product and silane compound to occur is not critical, but generally ranges from 5 minutes to 6 hours.

The amount of water used to create the aqueous phase or intermediate reaction product can vary, but is preferably based on the amount of the silane compound (III) used in the process. Water can be added directly, or indirectly, as some water may already be present in small amounts in other starting materials. For purposes of the present invention, it is preferable to calculate the total amount of water present, that is, accounting for all water added either directly or indirectly. Preferably, the total amount of water used to create the aqueous phase or the intermediate reaction product is 1 to 100 weight % of the silane compound used, with a range of 2.5 to 70 weight % being more preferred. Most preferred is a range of 20 to 40 weight % of water used for the intermediate reaction product based on the amount of silane compound used. Although not to be limited to any theory, the present inventors believe the addition of a buffer to the aqueous phase in the process to prepare sulfur containing organosilicon compounds using phase transfer catalysis helps to control the pH of the reaction medium, thereby affecting product formation and minimizing side reactions, such as the production of hydrogen sulfide; or the production of mercaptan silane having the general formula $(RO)_{3-m}R_mSi$—Alk—SH. Thus, as a second embodiment of the present invention, sulfur containing organosilicon compounds can be produced in the reaction described above by controlling the pH. The pH of the aqueous phase used in the reaction of the present invention can be controlled by the addition of a buffer, as described above, or alternatively, by the addition of any acidic or basic compounds at such a rate and concentration so as to maintain a pH during the reaction in the range of 7 to 14. The present inventors have also found that pH can have an influence on the product distribution, that is, the value of n in the product formula $(RO)_{3-m}R_mSi$—Alk—$S_n$—Alk—$SiR_m(OR)_{3-m}$. When the average value of n is desired to be 2 in the product formula, $(RO)_{3-m}R_mSi$—Alk—$S_n$—Alk—$SiR_m(OR)_{3-m}$, the preferred pH range is from 8 to 10. When the average value of n is desired to be 4 in the product formula, $(RO)_{3-m}R_mSi$—Alk—$S_n$—Alk—$SiR_m(OR)_{3-m}$, the preferred pH range is from 11 to 14.

The silane compound is added to the aqueous phase, or to the intermediate reaction product, as described above, at such a rate so as to control the exothermic reaction, and maintain a temperature in the range of 40 to 110° C. Preferably the reaction temperature is maintained at 60 to 95° C. The reaction progress can be monitored by the consumption of the silane compound starting material. The amount of catalyst and reaction temperature affects the reaction time necessary for completion.

At the end of the reaction, a product mixture is produced containing an organic phase, an aqueous phase, and possibly precipitated solid materials that can include salts such as NaCl, $Na_2HPO_4$, or $NaHCO_3$ (or analogous potassium salts) formed during the reaction. The organic phase contains the organosilane compound.

The present invention also encompasses processing steps to enhance the separation of the organosiloxane compound from the product mixture. This separation can be the phase separation of the organic and aqueous phase, resulting directly from the reaction of components (A), (B), and optional (C), as described above. Alternatively, if precipitated salts are formed during the reaction, the salts can be separated first by a filtering process or decanting method prior to the phase separation. Preferably, water or a dilute acidic solution is added to the product mixture prior to separation. The addition of water or a dilute acidic solution can enhance the phase separation by dissolving some or all of the precipitated salts. The amount of water or dilute acidic solution that is added during this step can vary from 10 to 50 weight % based on the weight of the amount of silane compound used, preferably, the amount of water or dilute acidic solution added is from 20 to 40 weight % based on the amount of the silane compound used, and most preferably from 25 weight % to 35 weight %. When a dilute acidic solution is used, it can be any of the common acids, for example HCl, $HNO_3$, $H_2SO_4$, or the like, having a normal (N) concentration of 0.000001 to 5, preferably 0.01 to 1. The dilute acidic solution can also be prepared by the addition of a chlorosilane to water. Examples of chlorosilanes that can be used to create the dilute acidic solution include trichlorosilane, trichloromethylsilane, dimethyldichlorosilane, dimethylchlorosilane, trimethylchlorosilane. Preferably, 0.5 to 10 weight % chlorosilane can be used to prepare the dilute acidic solution, with 1 to 5 weight % being the most preferred. When a chlorosilane is used to create the dilute acidic solution, the chlorosilane is preferably trimethylchlorosilane.

Following the addition of water or a dilute acidic solution to the product mixture, the organosilicon compound is isolated from the product mixture by phase separating the organic phase and aqueous phase. The organic phase containing the organosilicon compound can be further subjected to a drying step. One example of the drying step can be to treat the organic phase under vacuum to remove any volatile organic materials present along with any residual water that may be present. This drying step can involve, for example, heating the organic phase to a temperature of 20 to 160° C. under a reduced pressure of 5 to 35 mm Hg (0.67 to 4.65 kPa), preferably the conditions are 90 to 120° C. at 5 to 25 mm Hg (0.67 to 3.33 kPa). Alternatively, the drying step of the organic phase can involve the use of a thin film stripper to remove volatile organics materials and residual water content in the organic phase. Yet another technique for the drying step of the organic phase can be to contact the organic phase containing the organosilicon compound with a desiccant material. The desiccant material can be any solid material known in the art to remove trace quantities of water in organic phases. These include known ionic hygroscopic materials like sodium sulfate, magnesium sulfate, and the like, or silicate based materials such as zeolites, silica, aluminasilicates, and the like. The preferred desiccant material is either sodium sulfate or magnesium sulfate, with sodium sulfate being the most preferred.

The dried organic phase can be subjected to additional steps according to the present invention that result in further improvements of the organosilicon compound final purity and appearance. The organic phase containing the organosilicon compound can be cooled to a temperature below 15° C. This cooling step results in the precipitation of un-reacted sulfur and sulfur compounds. Preferably, the organic phase containing the organosilicon compound is cooled to a temperature in the range of −20 to 30° C., and most preferably to a temperature in the range of −15 and 15° C. The precipitated un-reacted sulfur and sulfur compounds can then be separated, for example by filtration, from the organic phase containing the organosilicon compound. The present inventors have found that removing un-reacted sulfur and sulfur compounds minimizes or eliminates further precipitation of sulfur and un-reacted sulfur compounds with time. As a result, the long-term storage stability of the organosilicon compound is enhanced by producing a composition that does not change with time or result in a product composition containing solid precipitates.

The following examples are provided to illustrate the present invention. These examples are not intended to limit the scope of the claims herein.

EXAMPLES

The distribution of the various sulfur containing organosilicon compounds were analyzed by high-pressure liquid chromatography (HPLC). Typical run conditions for HPLC analysis were as follows: 8–9 drops of the reaction sample were diluted in 8.5 g of cyclohexane, which was then filtered through a 0.2 µm PTFE membrane (e.g. PURADISC™ 25TF of Whatman®) into a vial, a 10 µl sample of the filtrate was injected via an autosampler into a HPLC system (e.g. Hewlett-Packard 1050). The sample was fractionated on a Lichrosorp RP18 column (e.g. Alltech Assoc., Inc; 250 mm×4.6 mm, 10 µm) using a mixture of 96% acetonitrile and 4% tetrahydrofurane (vol/vol) as mobile phase. The fractions were investigated via UV-absorption detector using 254 nm as the appropriate excitation wavelength. Different UV-sensitivities of every single sulfide species were averaged by division of the respective peak area through specific, empirically evaluated, response factors* (RF) listed below that reflect the hyperchromy with every sulfur atom in the chain and elemental sulfur.

As reported by H.-D. Luginsland, "Reactivity of the Sulfur Functions of the Disulfane Silane TESPD and the Tetrasulfane Silane TESPT"; Rubber Division, American Chemical Society; Chicago, Ill., Apr. 13–16, 1999.

HPLC Response Factors

| S2 | S3 | S4 | S5 | S6 | S7 | S8 | S9 | S10 | $S_{elem.}$ |
|---|---|---|---|---|---|---|---|---|---|
| 1.0 | 3.52 | 6.39 | 9.78 | 13.04 | 17.39 | 20.87 | 26.08 | 31.30 | 37.26 |

Comparative Example

A 100-ml-flask, equipped with magnetic stir bar and internal thermometer was loaded at 76 degrees Celsius with 6.75 g of disodium sulfide (59.75% $Na_2S$, 0.26% NaHS), and 2.08 g of elemental sulfur. Then, 6.25 g of water were added and the mixture stirred until all solids were dissolved. Then, 1.00 g of a 25% aqueous catalyst solution (0.25 g of tetrabutyl ammonium bromide in 0.75 g of water) was added. Then 6.03 g of chloropropyltriethoxysilane were added via syringe in 1 mL portions. Within 20 minutes, the reaction temperature increased to 80 degrees Celsius and the mixture immediately solidified to form an orange-brown gel. Further addition of chloropropyltriethoxysilane resulted in the formation of a white resin on top of the gel.

Example 1

A 100-ml-flask, equipped with magnetic stir bar, condenser and internal thermometer, was loaded at 78 degrees Celsius with 4.01 g of flaked sodium hydrogen sulfide (2.08% $Na_2S$, 71.10% NaHS), 1.66 g of elemental sulfur and 7.37 g of disodium sulfate. 12.50 g of water were added and the mixture was stirred until all solids were dissolved. Strong formation of dihydrogen sulfide gas was observed.

1.00 g of a 25% aqueous catalyst solution (0.25 g of tetrabutyl ammonium bromide in 0.75 g of water) was added. Then 23.75 g of chloropropyltriethoxysilane were added via syringe within 40 minutes in portions of 2 ml. The reaction temperature increased to 79 degrees Celsius. After the decrease of the exotherm, the mixture was stirred at a temperature of 78 degrees Celsius, and the reaction progress was followed by quantitative gas chromatography analysis until chloropropyltriethoxysilane had reached a stable level after 2.75 hours. The reaction mixture was cooled to room temperature and 20.18 g of a clear and nearly colorless liquid were collected via pipette from top of the aqueous phase. High pressure liquid chromatography analysis showed an average sulfur rank of 3.11. Quantitative gas chromatography analysis showed 36.45% un-reacted chloropropyltriethoxysilane.

Example 2

A 100-ml-flask, equipped with magnetic stir bar, condenser and internal thermometer, was loaded at 76 degrees Celsius with 4.01 g of flaked sodium hydrogen sulfide (2.08% $Na_2S$, 71.10% NaHS), 1.66 g of elemental sulfur and 10.45 g of disodium tetraborate ($Na_2B_4O_7$). 12.50 g of water were added and the mixture was stirred until all solids were dissolved. Slight formation of dihydrogen sulfide gas was observed. 1.00 g of a 25% aqueous catalyst solution (0.25 g of tetrabutyl ammonium bromide in 0.75 g of water) was added. Then 23.75 g of chloropropyltriethoxysilane were added via syringe within 44 minutes in portions of 2 ml every four minutes. The reaction temperature increased to 78 degrees Celsius. After the decrease of the exotherm, the mixture was stirred at a temperature of 76 degrees Celsius, and the reaction progress was followed by quantitative gas chromatography analysis until chloropropyltriethoxysilane had reached a stable ratio level after 3 hours. The reaction mixture was cooled to room temperature and 22.88 g of a clear and nearly colorless liquid were collected via pipette from top of the aqueous phase. High pressure liquid chromatography analysis showed an average sulfur rank of 2.53. Quantitative gas chromatography analysis showed 21.03% unreactedchloropropyltriethoxysilane.

Example 3

A 100-ml-flask, equipped with magnetic stir bar, condenser and internal thermometer, was loaded at 78 degrees Celsius with 4.01 g of flaked sodium hydrogen sulfide (2.08% $Na_2S$, 71.10% NaHS), 1.66 g of elemental sulfur and 5.51 g of disodium carbonate. Then, 18.75 g of water were added and the mixture was stirred until all solids were dissolved. Then, 1.00 g of a 25% aqueous catalyst solution (0.25 g of tetrabutyl ammonium bromide in 0.75 g of water) was added. Then 23.75 g of chloropropyltriethoxysilane were added via syringe within 33 minutes in portions of 2 ml every three minutes. The reaction temperature increased to 80 degrees Celsius. After the decrease of the exotherm, the mixture was stirred at a temperature of 79 degrees Celsius, and the reaction progress was followed by quantitative gas chromatography analysis until chloropropyltriethoxysilane has reached a stabile ratio level after 3.25 hours. The reaction mixture was cooled down to 50 degrees Celsius and 9.73 g of water were added. The mixture was stirred until all formed salts were dissolved. The mixture was cooled to 30 degrees Celsius and 22.64 g of a clear and nearly colorless liquid were collected via pipette from top of the aqueous phase. High pressure liquid chromatography analysis showed an average sulfur rank of 2.16. Quantitative gas chromatography analysis showed 3.46% un-reacted chloropropyltriethoxysilane.

Example 4

A 100-ml-flask, equipped with magnetic stir bar, condenser and internal thermometer, was loaded at 74 degrees Celsius with 4.01 g of flaked sodium hydrogen sulfide (2.08% $Na_2S$, 71.10% NaHS), 1.66 g of elemental sulfur and 8.51 g of trisodium phosphate. Then, 12.50 g of water were added and the mixture was stirred until all solids were dissolved. Then, 1.00 g of a 25% aqueous catalyst solution (0.25 g of tetrabutyl ammonium bromide in 0.75 g of water) was added. Then 24.00 g of chloropropyltriethoxysilane were added via syringe within 33 minutes in portions of 2 ml every three minutes. The reaction temperature increased to 78 degrees Celsius. After the decrease of the exotherm, the mixture was stirred at a temperature of 76 degrees Celsius, and the reaction progress was followed by quantitative gas chromatography analysis until chloropropyltriethoxysilane had reached a stable ratio level after 2.75 hours. The reaction mixture was cooled down to room temperature and 21.14 g of a clear and nearly colorless liquid were collected via pipette from top of the aqueous phase. High pressure liquid chromatography analysis showed an average sulfur rank of 2.12. Quantitative gas chromatography analysis showed 1.66% un-reacted chloropropyltriethoxysilane.

Example 5

A 1-1-reactor, equipped with mechanical stirrer, 1 baffle, condenser, dropping funnel, and internal thermometer, was loaded at 74 degrees Celsius with 72.18 g of flaked sodium hydrogen sulfide (2.08% $Na_2S$, 71.10% NaHS), 29.94 g of elemental sulfur and 153.00 g of trisodium phosphate. Then, 225 g of water were added and the mixture was vigorously stirred until all solids were dissolved. Then, 18.00 g of a 25% aqueous catalyst solution (4.50 g of tetrabutyl ammonium bromide in 13.50 g of water) were added. Then 427.50 g of chloropropyltriethoxysilane were added within 70 minutes and the reaction temperature raised to 82 degrees Celsius. After the decrease of the exotherm, the mixture was stirred at a temperature of 79 degrees Celsius, and the reaction progress was followed by gas chromatography analysis until chloropropyltriethoxysilane had reached a stable ratio level after 2.75 hours. The mixture was cooled to 50 degrees Celsius when 150 g of water were added. The mixture was further cooled to 30 degrees Celsius and another 25.0 g of water were added. The mixture was stirred until all formed salts were dissolved. Then, 664.65 g of a clear, colorless aqueous phase were drained off. The remaining organic phase was also drained off and without further purification 419.81 g of a clear, light yellow liquid were received. High pressure liquid chromatography analysis showed an average sulfur rank of 2.12. Quantitative gas chromatography analysis showed 0.73% un-reacted chloropropyltriethoxysilane.

Example 6

A 100-ml-flask, equipped with magnetic stir bar, condenser and internal thermometer, was loaded at 76 degrees Celsius with 4.01 g of flaked sodium hydrogen sulfide (2.08% $Na_2S$, 71.10% NaHS), 4.99 g of elemental sulfur and 8.51 g of trisodium phosphate. Then, 12.50 g of water were added and the mixture was stirred until all solids were dissolved. Then, 1.00 g of a 25% aqueous catalyst solution (0.25 g of tetrabutyl ammonium bromide in 0.75 g of water) was added. Then 24.00 g of chloropropyltriethoxysilane were added via syringe within 36 minutes in portions of 2 ml every three minutes. The reaction temperature increased to 79 degrees Celsius. After the decrease of the exotherm, the mixture was stirred at a temperature of 78 degrees Celsius, and the reaction progress was followed by quantitative gas chromatography analysis until chloropropyltriethoxysilane has reached a stable ratio level after 4 hours. The reaction mixture was cooled to 50 degrees C., when 9.72 g of water were added to dissolve the sodium chloride. The mixture was cooled to room temperature and 24.38 g of a orange-brown liquid were collected via pipette from top of the aqueous phase. High pressure liquid chromatography analysis showed an average sulfur rank of 3.86.

Example 7

A 1-1reactor, equipped with mechanical stirrer, 1 baffle, condenser, dropping funnel, and internal thermometer, was loaded at 76 degrees Celsius with 450.00 g of water. Then, 153.13 g of trisodium phosphate and 132.63 g of disodium hydrogen phosphate were added in portions. The mixture was vigorously stirred until all salts were dissolved. Then, 38.01 g of an aqueous solution of sodium hydrogen sulfide (0.24% $Na_2S$, 45.77% NaHS) were added. Then, 9.98 g of elemental sulfur were added and the mixture was stirred until a clear, dark amber solution was formed. 4.00 g of a 25% aqueous catalyst solution (1.00 g of tetrabutyl ammonium bromide in 3.00 g of water) were added. Then 150.00 g of chloropropyltriethoxysilane were added within 15 minutes and the reaction temperature increased to 79.5 degrees Celsius. Another 2.00 g of the 25% aqueous catalyst solution (1.00 g of tetrabutyl ammonium bromide in 3.00 g of water) were added. After the decrease of the exotherm, the mixture was stirred at a temperature of 76 degrees Celsius, and the reaction progress was followed by gas chromatography analysis until chloropropyltriethoxysilane has reached a stable ratio level after 2.5 hours. Then, 787.77 g of clear colorless aqueous phase were drained off. The remaining organic phase was cooled down to 15 degrees Celsius, drained off (132.01 g raw material) and filtered in a Büchner funnel through Paper (e.g. Whatman® 1) to yield 127.18 g of a clear, light yellow liquid. High pressure liquid chromatography analysis showed an average sulfur rank of 2.04. Quantitative gas chromatography analysis showed 0.65% un-reacted chloropropyltriethoxykysilane.

Example 8

A 1-1-reactor, equipped with mechanical stirrer, 1 baffle, condenser, dropping funnel, and internal thermometer, was loaded at 76 degrees Celsius with 450.00 g of water. 102.12 g of trisodium phosphate and 176.84 g of disodium hydrogen phosphate were added in portions. The mixture was vigorously stirred until all salts were dissolved. Then, 38.01 g of an aqueous solution of sodium hydrogen sulfide (0.24% $Na_2S$, 45.77% NaHS) were added. Then, 9.98 g of elemental sulfur were added and the mixture was stirred until a clear, dark amber solution was formed. 4.00 g of a 25% aqueous catalyst solution (1.00 g of tetrabutyl ammonium bromide in 3.00 g of water) were added. Then 150.00 g of chloropropyltriethoxysilane were added within 15 minutes and the reaction temperature increased to 79.0 degrees Celsius. Another 2.00 g of the 25% aqueous catalyst solution (1.00 g of tetrabutyl ammonium bromide in 3.00 g of water) were added. After the decrease of the exotherm, the mixture was stirred at a temperature of 76 degrees Celsius, and the reaction progress was followed by gas chromatography analysis until chloropropyltriethoxysilane had reached a stable ratio level after 3 hours. Then, 771.09 g of clear colorless aqueous phase were drained off. The remaining organic phase was cooled to 15 degrees Celsius, drained off (133.82 g raw material) and filtered in a Büchner funnel through Paper (e.g. Whatman® 1) to yield 130.08 g of a clear, light yellow liquid. High pressure liquid chromatography analysis showed an average sulfur rank of 2.05. Quantitative gas chromatography analysis showed 1.07% un-reacted chloropropyltriethoxysilane.

Example 9

A 1-1-reactor, equipped with mechanical stirrer, 1 baffle, condenser, dropping funnel, and internal thermometer, was loaded at 76 degrees Celsius with 450.00 g of water. 51.06 g of trisodium phosphate and 221.05 g of disodium hydrogen phosphate were added in portions. The mixture was vigorously stirred until all salts were dissolved. Then, 38.01 g of an aqueous solution of sodium hydrogen sulfide (0.24% $Na_2S$, 45.77% NaHS) were added. Then, 9.98 g of elemental sulfur were added and the mixture was stirred until a clear, dark amber solution was formed. Then, 4.00 g of a 25% aqueous catalyst solution (1.00 g of tetrabutyl ammonium bromide in 3.00 g of water) were added. Then 150.00 g of chloropropyltriethoxysilane were added within 15 minutes and the reaction temperature increased to 79.0 degrees Celsius. Another 2.00 g of the 25% aqueous catalyst solution (1.00 g of tetrabutyl ammonium bromide in 3.00 g of water) were added. After the decrease of the exotherm, the mixture was stirred at a temperature of 76 degrees Celsius, and the reaction progress was followed by gas chromatography analysis until chloropropyltriethoxysilane had reached a stable ratio level after 3.5 hours. Then 762.30 g of a clear colorless aqueous phase were drained off The remaining organic phase was cooled to 15 degrees Celsius, drained off (143.04 g raw material) and filtered in a Büchner funnel through Paper (e.g. Whatman® 1) to yield 141.18 g of a clear, light yellow liquid. High pressure liquid chromatography analysis showed an average sulfur rank of 2.09. Quantitative gas chromatography analysis showed 2.77% un-reacted chloropropyltriethoxysilane.

Example 10

A 1-1-reactor, equipped with mechanical stirrer, 1 baffle, condenser, dropping funnel and internal thermometer, was loaded at 76 degrees Celsius with 450.00 g of water. Then, 265.26 g of disodium hydrogen phosphate were added in portions. The mixture was vigorously stirred until all salts were dissolved. Then, 38.01 g of an aqueous solution of sodium hydrogen sulfide (0.24% $Na_2S$, 45.77% NaHS) were added. Then, 9.98 g of elemental sulfur were added and the mixture was stirred until a clear, dark amber solution was formed. Then, 4.00 g of a 25% aqueous catalyst solution (1.00 g of tetrabutyl ammonium bromide in 3.00 g of water) were added. Then 150.00 g of chloropropyltriethoxysilane were added within 15 minutes and the reaction temperature raised to 79.0 degrees Celsius. Another 2.00 g of the 25% aqueous catalyst solution (1.00 g of tetrabutyl ammonium bromide in 3.00 g of water) were added. After the decrease of the exotherm, the mixture was stirred at a temperature of 76 degrees Celsius, and the reaction progress was followed by gas chromatography analysis until chloropropyltriethoxysilane had reached a stable ratio level after 4.5 hours. Then, 756.55 g of a clear colorless aqueous phase were drained off. The remaining organic phase was cooled to 15 degrees Celsius, drained off (143.49 g raw material) and filtered in a is Büchner funnel through Paper (e.g. Whatman® 1) to yield 140.48 g of a clear, light yellow liquid. High pressure liquid chromatography analysis showed an average sulfur rank of 2.19. Quantitative gas chromatography analysis showed 11.92% un-reacted chloropropyltriethoxysilane.

Example 11

A jacketed 1.5 L reactor equipped with a mechanical stirrer, 1 baffle, and an internal thermocouple was charged at room temperature with 419.81 g of water. Then, 151.33 g solid K$_2$CO$_3$, 134.85 g aqueous NaSH solution (45.85 wt % NaSH) and 34.96 g sulfur powder were charged to the reactor with mixing. The reactor contents were then heated to 70° C., after holding at 70° C. for 5 minutes, 21.01 g of a 25 wt % aqueous tetrabutylammoniumbromide (TBAB) solution was charged to the reactor and allowed to mix for 10–15 minutes. Then, 500.02 g. of chloropropyltriethoxysilane (CPTES) was charged to the reactor dropwise via an addition funnel. The CPTES addition rate was limited by the cooling jacket capability and a desire to maintain the reactor temperature below 85 C. After the addition of CPTES, the reactor was held at 75° C. for 2 to 3.5 hours until the reaction was determined to be complete, as determined by no further conversion of CPTES as measured by gas chromatographic analysis of the organic phase. After the reaction was complete, the reactor was cooled to 50° C. and water was added to the reactor to dissolve the salts present in the reactor. Agitation was then stopped and the reactor contents allowed to phase separate. The lower aqueous phase was then drained off, leaving behind 458.9 g. of product. Un-reacted CPTES and other low boiling impurities (2.50 wt % of the crude product) were removed by vacuum stripping leaving behind a final product, ((EtO)$_3$SiCH$_2$CH$_2$CH$_2$)$_2$S$_x$, with x=2.12.

Example 12

A jacketed 1.5 L reactor equipped with a mechanical stirrer, 1 baffle, and an internal thermocouple was charged at room temperature with 50.56 g of water. Then, 317.8 g of an 47.6 wt % aqueous K$_2$CO$_3$ solution, 135.09 g aqueous NaSH solution (45.56 wt % NaSH) and 37.04 g sulfur flakes were charged to the reactor with mixing. The reactor contents were then heated to 70° C. After holding at 70° C. for 5 minutes, 20.99 g of a 25 wt % aqueous tetrabutylammoniumbromide (TBAB) solution was charged to the reactor and allowed to mix for 10–15 minutes. Then, 500.02 g. of chloropropyltriethoxysilane (CPTES) was charged to the reactor dropwise via an addition funnel. The CPTES addition rate was limited by the cooling jacket capability and a desire to maintain the reactor temperature below 85° C. After the addition of CPTES, the reactor was held at 75° C. for 2 to 3.5 hours until the reaction was determined to be complete, as determined by no further conversion of CPTES, as measured by gas chromatographic analysis of the organic phase. After the reaction was complete, the reactor was cooled to 50° C. and water was added to the reactor to dissolve the salts present in the reactor. Agitation was then stopped and the reactor contents allowed to phase separate. The lower aqueous phase was then drained off, leaving behind 479.1 g. of product. Unreacted CPTES and low boiling impurities (1.77 wt % of the crude product) were removed by vacuum stripping leaving behind a final product, ((EtO)$_3$SiCH$_2$CH$_2$CH$_2$)$_2$S$_x$, with x=2.16.

We claim:

1. A process for the production of organosilicon compounds of the formula:

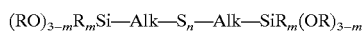

where
R is independently a monovalent hydrocarbon of 1 to 12 carbon atoms; Alk is a divalent hydrocarbon of 1 to 18 carbon atoms;
m is an integer of 0 to 2, n is a number from 1 to 8;
comprising reacting:
(A) a sulfide compound having the formula M$_2$S$_n$ or MHS,
where H is hydrogen, M is ammonium or an alkali metal,
n is as defined above, with
(B) a silane compound of the formula;

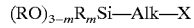

where X is Cl, Br or I, and m is the same as above, and optionally,
(C) sulfur
in the presence of a phase transfer catalyst and an aqueous phase containing a buffer.

2. The process of claim 1 wherein the buffer is an alkali metal salt of a phosphate, a hydrogen phosphate, a dihydrogen phosphate, a carbonate, a hydrogen carbonate, or a borate.

3. The process of claim 1 wherein the buffer is selected from Na$_3$PO$_4$, Na$_2$HPO$_4$, NaH$_2$PO$_4$, Na$_2$CO$_3$, NaHCO$_3$, K$_2$CO$_3$, or NaB$_4$O$_7$.

4. The process of claim 3 wherein the buffer is Na$_3$PO$_4$.

5. The process of claim 3 wherein the buffer is Na$_2$CO$_3$.

6. The process of claim 3 wherein the buffer is K$_2$CO$_3$.

7. The process of claim 3 wherein the molar concentration of buffer in the aqueous phase is at least equal to the number of moles of M$_2$S$_n$ or MHS present.

8. The process of claim 1 wherein the weight percent of the phase transfer catalyst to the silane compound is 0.1 to 10%.

9. The process of claim 1 wherein the weight percent of the phase transfer catalyst to the silane compound is 0.5 to 3%.

10. The process of claim 1 wherein there is a 2.0 to 2.1 molar excess of the (RO)$_{3-m}$R$_m$Si—Alk—X silane compound to the sulfide compound.

11. The process of claim 1 wherein the molar ratio of sulfur to the sulfide compound is 0.3 to 5.

12. The process of claim 1 wherein the molar ratio of sulfur to the sulfide compound is 2.7 to 3.2.

13. The process of claim 1 wherein the weight percentage of water in the aqueous phase to the silane compound is 2.5 to 70%.

14. The process of claim 1 wherein the weight percentage of water in the aqueous phase to the silane compound is 20 to 40%.

15. The process of claim 1 wherein the silane compound is selected from chloropropyl triethoxy silane, chloropropyl trimethoxy silane, chloroethyl triethoxy silane, chlorobutyl triethoxy silane, chloroisobutylmethyl diethoxy silane, chloroisobutylmethyl dimethoxy silane, and chloropropyldimethyl ethoxy silane.

16. The process of claim 15 wherein the silane compound is chloropropyl triethoxy silane.

17. The process of claim 1 wherein the sulfide compound is selected from Na$_2$S, K$_2$S, Cs$_2$S, (NH$_4$)$_2$S, Na$_2$S$_2$, Na$_2$S$_3$, Na$_2$S$_4$, Na$_2$S$_6$, K$_2$S$_2$ K$_2$S$_3$, K$_2$S$_4$, K$_2$S$_6$, and (NH$_4$)$_2$S$_2$.

18. The process of claim 17 wherein the sulfide compound is Na$_2$S.

19. The process of claim 1 wherein the sulfide compound is selected from NaHS, KHS, and N$_4$HS.

20. The process of claim 19 wherein the sulfide compound is NaHS.

21. The process of claim 1 wherein the phase transfer catalyst is a quaternary onium salt.

22. The process of claim 21 wherein the phase transfer catalyst is tetrabutyl ammonium bromide.

23. A process for the production of organosilicon compounds of the formula $$(RO)_{3-m}R_mSi—Alk—S_n—Alk—SiR_m(OR)_{3-m}$$

where R is independently a monovalent hydrocarbon of 1 to 12 carbon
atoms; Alk is a divalent hydrocarbon of 1 to 18 carbon atoms;
m is an integer of 0 to 2, n is a number from 1 to 8,
comprising:
(A) reacting, a phase transfer catalyst, a sulfide compound having the formula $M_2S_n$ or MHS,
where H is hydrogen, M is ammonium or an alkali metal, n is the same as above, water, a buffer and, optionally sulfur, to form an intermediate reaction product;
(B) reacting said intermediate reaction product with a silane compound of the formula;

$$(RO)_{3-m}R_mSi—Alk—X$$

where X is Cl, Br or I, and m is the same as above.

24. The process of claim 23 wherein the silane compound is dispersed in an organic solvent selected from toluene, xylene, benzene, heptane, octane, decane, and chlorobenzene.

25. The process of claim 24 wherein the organic solvent is toluene.

26. The process of claim 23 wherein the reaction of said intermediate reaction product with the silane compound is conducted at a temperature in the range of 40 to 110° C.

27. The process of claim 23 wherein the reaction of said intermediate reaction product with the organic phase containing the silane compound is conducted at a temperature in the range of 60 to 95° C.

28. A process for the production of organosilicon compounds of the formula:

$$(RO)_{3-m}R_mSi—Alk—S_n—Alk—SiR_m(OR)_{3-m}$$

where
R is independently a monovalent hydrocarbon of 1 to 12 carbon atoms; Alk is a divalent hydrocarbon of 1 to 18 carbon atoms;
m is an integer of 0 to 2, n is a number from 1 to 8;
comprising
(I) reacting:
(A) a sulfide compound having the formula $M_2S_n$ or MHS,
where H is hydrogen, M is ammonium or an alkali metal,
n is as defined above, with
(B) a silane compound of the formula;

$$(RO)_{3-m}R_mSi—Alk—X$$

where X is Cl, Br or I, and m is the same as above, and optionally,
(C) sulfur
in the presence of a phase transfer catalyst and an aqueous phase containing a buffer to form a product mixture,
(II) separating the organosilicon compound from the product mixture.

29. The process of claim 28 wherein the organosilicon compound is separated from the product mixture by
(D) adding water or a dilute acidic solution to the product mixture, and
(E) phase separating the product mixture into an organic phase containing the organosilicon compound and an aqueous phase.

30. The process of claim 28 wherein the weight percentage of water or dilute acidic solution to the silane compound is 10–50%.

31. The process of claim 28 wherein the weight percentage of water or dilute acidic solution to the silane compound is 20–40%.

32. The process of claim 28 wherein the organic phase containing the organosilicon compound is dried.

33. The process of claim 32 wherein the organic phase containing the organosilicon compound is dried by heating the organic phase at reduced pressures.

34. The process of claim 32 wherein the organic phase containing the organosilicon compound is dried by contacting the organic phase with a solid desiccant.

35. The process of claim 34 wherein the solid desiccant is sodium sulfate or magnesium sulfate.

36. The process of claim 35 wherein the desiccant is sodium sulfate.

37. The process of claim 28 further comprising the steps;
(F) cooling the organic phase containing the organosilicon compound below 15° C. to precipitate un-reacted sulfur compounds,
(G) separating the organic phase containing the organosilicon compound from the precipitated un-reacted sulfur compounds.

38. The process of claim 37 wherein the organic phase containing the organosilicon compound is cooled to a temperature in the range of –20 to 10° C.

39. The process of claim 37 wherein the organic phase containing the organosilicon compound is cooled to a temperature in the range of –15 to –10° C.

* * * * *